United States Patent [19]

Celmer et al.

[11] Patent Number: 4,543,334
[45] Date of Patent: Sep. 24, 1985

[54] STREPTOMYCES CAPABLE OF PRODUCING NEUTRAL MACROLIDE ANTIBACTERIAL AGENTS

[75] Inventors: Walter D. Celmer, New London; Walter P. Cullen, East Lyme, both of Conn.; Hiroshi Maeda, Aichi; Junsuke Tone, Chita, both of Japan

[73] Assignee: Pfizer Inc., New York, N.Y.

[21] Appl. No.: 562,784

[22] Filed: Dec. 16, 1983

[51] Int. Cl.$^4$ ............... C12N 1/20; C12R 1/465; C12P 19/62; C07J 00/00
[52] U.S. Cl. ................ 435/253; 435/76; 435/886; 536/7.1
[58] Field of Search .............. 435/253, 124, 886, 76

[56] References Cited

U.S. PATENT DOCUMENTS 3,857,937 12/1974 Mancy et al. ............... 424/120
4,169,140 9/1979 Ohba et al. ............... 424/117

OTHER PUBLICATIONS

Arnoux, et al., J. Am. Chem. Soc., 102, 3605 (1980).

*Primary Examiner*—Alvin E. Tanenholtz
*Attorney, Agent, or Firm*—Charles J. Knuth; Albert E. Frost; James M. McManus

[57] ABSTRACT

An antibiotic complex, consisting of one major and two minor components, has been isolated from fermentation of a new Streptomyces culture. The components from the complex are three new macrolides which are active as antibacterial agents against certain gram-negative and gram-positive microorganisms.

1 Claim, No Drawings

STREPTOMYCES CAPABLE OF PRODUCING NEUTRAL MACROLIDE ANTIBACTERIAL AGENTS

BACKGROUND OF THE INVENTION

This invention relates to a new antibiotic complex made up of one major and two minor components, which are derived from fermentation of a new Streptomyces culture, designated N469-34, obtained from a soil sample from Georgia, U.S.A. The three components of the complex are macrolides and differ from other macrolides in that they are neutral macrolides, have a new keto sugar and contain a new 2-hydroxyisovaleryl moiety in their structure.

SUMMARY OF THE INVENTION

This invention provides new macrolide antibiotic compounds selected from the group consisting of

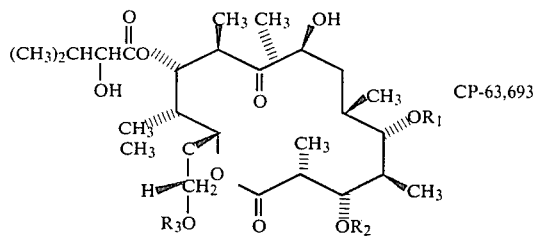
CP-63,693   I

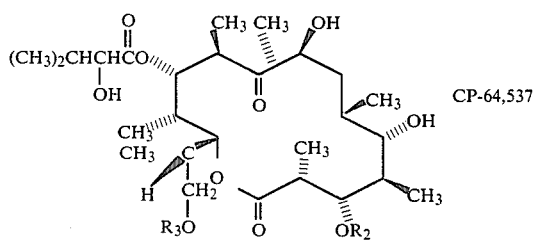
CP-64,537   II and

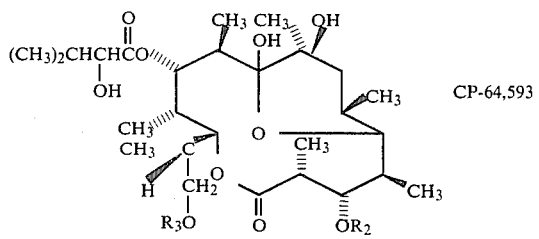
CP-64,593   III wherein $R_1$ is the group of the formula

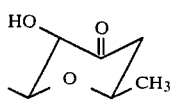

$R_2$ is the group of the formula

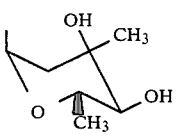

and $R_3$ is the group of the formula

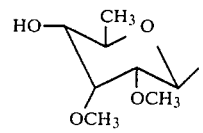

These neutral macrolides are useful as anti-bacterial agents, and are obtained by fermentation of a new Streptomyces culture identified as *Streptomyces toyocaensis* subsp. *humicola* Huang subsp. nov. designated culture N469-34 (ATCC 39471).

Especially preferred for its antibacterial activity is CP-63,693, the major component of the aforementioned complex.

DETAILED DESCRIPTION OF THE INVENTION

The antibiotic complex of the present invention is produced by fermentation of a new microorganism designated as culture N469-34, which was obtained from a soil sample collected in Stone Mountain Park, Ga., U.S.A. Culture N469-34 was characterized and identified by Liang H. Huang, Ph.D., Pfizer Inc., Groton, Conn., U.S.A., as described hereinbelow.

On examination, culture N469-34 possessed narrow hyphae of the Actinomycetales, spore chains produced on the aerial mycelium and an unfragmented substrate mycelium, a feature characteristic of members of Streptomyces.

Culture N469-34 was planted from a slant into ATCC No. 172 broth and grown for four days at 28° C. on a shaker. It was then centrifuged for 20 minutes, washed three times with sterile distilled water and planted on media commonly used for identification of members of the Actinomycetales.

Culture N469-34 was incubated at 28° C. and results being read at varying times, but most commonly at 14 days. Colors used to describe culture N469-34 are described in common terminology, but exact colors are determined by comparisons with color chips from the "Color Harmony Manual", 4th edition. The methods of whole-cell amino acid and sugar analyses are those described in Becker, B. et al., Appl. Microbiol., 12: 421–423, 1964, and in Lechevalier, M. P., J. Lab. Clin. Med., 71: 934–944, 1968. For the purpose of comparisons, *Streptomyces toyocaensis* ATCC 19814 was purchased from American Type Culture Collection, Rockville, Md.

Identification media used for the characterization of the culture and references for their composition are as follows:
1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium no. 1, p. 328, 1961.

8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no. 14, p. 330.
12. Gordon and Smith's Tyrosine Agar—R. E. Gordon and M. M. Smith, Jr., Bact., 69: 147–150, 1955.
13. Casein Agar—Ibid.
14. Calcium Malate Agar—S. A. Waksman, Bact. Rev., 21: 1–29, 1957.
15. Gelatin—R. E. Gordon and J. M. Mihm, Jr., Bact., 73: 15–27, 1957.
16. Starch—Ibid.
17. Organic Nitrate Broth—Ibid.
18. Dextrose Nitrate Broth—S. A. Waksman, The Actinomycetes, Vol. 2, medium no. 1, p. 328, 1961, with 3 g. dextrose substituted for 30 g. sucrose and agar omitted.
19. Potato Carrot Agar—M. P. Lechevalier, Jr. Lab. and Clinical Med., 71: 934–944, 1968, but use only 30 g. potatoes, 2.5 g. carrots and 20 g. agar.
20. 2% Tap Water Agar.
21. Skim Milk—Difco.
22. Cellulose Utilization
   (a) H. L. Jensen, Proc. Linn, Soc. N.S.W., 55: 231–248, 1930.
   (b) M. Levine and H. W. Schoenlein, A Compilation of Culture Media, medium no. 2511, 1930.
23. Carbohydrates—ISP #9 medium, Difco.
24. Temperature Range—ISP #2 medium plus 50 ml. coconut milk.

Yeast Extract-Malt Extract Agar—Growth good, white to gray (near gray series 2dc, 2fe, 3fe, 2ih), raised, slightly wrinkled, with white to gray aerial mycelium; reverse yellowish brown (3gc, 21c) with gray dots (2ge); no soluble pigment.

Oatmeal Agar—Growth moderate, pink gray (near gray series 3fe, 5fe, 5ih) with white dots, thin to slightly raised, smooth to granular, aerial mycelium white to pink gray; reverse colorless, cream (1½ca) to pale grayish (near gray series 2fe, 3fe); soluble pigment none to very pale yellowish (near gray series 1ba).

Inorganic Salts-Starch Agar—Growth good, pink gray (near gray series 3fe, 5fe, 5ih) with white dots, moderately raised, slightly wrinkled, aerial mycelium white to pink gray; reverse gray (near gray series 3fe, 3ih); soluble pigment none to very pale yellowish (1½ca).

Glycerol-Asparagine Agar—Growth poor to moderate with dots of cream growth (1½ca), thin to slightly raised, no aerial mycelium; reverse cream (1½ca); no soluble pigment.

Czapek-Sucrose Agar—Growth poor to moderate, colorless to pale gray (near gray series 3dc, 3fe), thin, smooth, with a few white to pale gray dots, aerial mycelium white to pale gray; reverse colorless or pale gray (near gray series 3dc, 3fe); no soluble pigment.

Glucose-Asparagine Agar—Growth moderate to good, white to pink gray (near gray series 3fe, 3ih, 5fe, 5ih), granular to slightly wrinkled, moderately raised, aerial mycelium white to pink gray; reverse cream to pale yellow (1½ca, 1½ea) with pale gray dots (near gray series 3dc); soluble pigment none to very pale yellow (near gray series 1ba).

Gordon and Smith's Tyrosine Agar—Growth good, cream (1½ca), slightly to moderately raised, smooth, no aerial mycelium; reverse same as surface; soluble pigment pale yellow (2ea).

Calcium Malate Agar—Growth moderate, white to cream (1½ca), thin to raised, smooth to granular, aerial mycelium white; reverse colorless to cream (1½ca); soluble pigment none to pale yellowish (near gray series 1ba).

Casein Agar—Growth good, cream (2ca), slightly to moderately raised, smooth to slightly wrinkled, no aerial mycelium; reverse yellowish to yellowish brown (21c); soluble pigment lavender pink (4gc).

Bennett's Agar—Growth good, white to pink gray (near gray series 3fe, 5fe, 5ih), raised, wrinkled, aerial mycelium white to pink gray; reverse yellow, pale yellowish to grayish yellow (2ea, 21e); soluble pigment pale yellow (2ea, 2ga).

Emerson's Agar—Growth good, grayish yellow (2gc), raised, smooth to wrinkled, no aerial mycelium; reverse same as surface; soluble pigment yellowish brown (31c).

Nutrient Agar—Growth moderate to good, cream (2ca), slightly raised, smooth, no aerial mycelium; reverse pale yellow (2ea); no soluble pigment.

Gelatin Agar—Growth good, cream (1½ca), raised, smooth to slightly wrinkled, no aerial mycelium; reverse cream; no soluble pigment.

Starch Agar—Growth good, cream (1½ca), raised, smooth to slightly wrinkled; aerial mycelium none to sparse, white; reverse cream; no soluble pigment.

Potato Carrot Agar—Growth poor to moderate, cream (near gray series 1ba); appearing as smooth, isolated, small colonies; thin to slightly raised; with sparse, white aerial mycelium; reverse colorless to cream; no soluble pigment.

Tap Water Agar—Growth poor, colorless to pale gray (near gray series 3cb, 3dc, 2dc), thin, smooth; or appearing as small, isolated colonies; aerial mycelium pale gray; reverse same as surface; no soluble pigment.

Morphological Properties—The morphological observations were made on inorganic salts-starch agar after 14 days of incubation; spore mass in Gray-color series; spore chains mostly spiral, rarely hooked or looped, arranged in tight coils, 3 to 7 coils per spore chain, often coiled into compact masses of different shapes, 10 to 50 spores per spore chain; sporophores monopodially branched; spores globose to oval, sometimes elliptical, 0.9–1.4 μm in diam., or 1.1–1.5(–1.8)×0.9–1.1 μm; spiny, as revealed by scanning electron microscopy.

Biochemical Properties—Melanin not produced; hydrogen sulfide not produced; gelatin liquefied; starch hydrolyzed; nitrate not reduced to nitrite; some growth on Jensen's broth but no growth on Levine and Schoenlein's broth; no decomposition on both cellulose broths; clearing and coagulation on milk; casein digestion positive; calcium malate digestion positive; tyrosine digestion positive. Carbohydrate utilization: glucose, arabinose, fructose, inositol, mannitol, raffinose, and sucrose utilized; xylose and rhamnose not utilized.

Temperature Relations

| 21° C. | 28° C. | 37° C. | 45° C. |
| --- | --- | --- | --- |
| Good Growth | Good Growth | Moderate to Good Growth | No Growth |

Cell Wall Analysis—The whole-cell hydrolysates contain LL-diaminopimelic acid but no characteristic sugars.

Culture N469-34 is distinguished by its gray spore masses, negative melanin reaction, spiral spore chains, and spores with a spiny surface. When compared with related species of Streptomyces, it closely resembles *S. toyocaensis* Nishimura, Katagiri, Sato, Mayama & Shimaoka described in Japanese Patent No. 236280 (1954) and in Shirling, E. B. and Gottlieb, D., Int. J. Syst. Bacteriol. 18:69–189, 1968. When compared with each other, both cultures show a similar morphology and share many of cultural and biochemical properties in common. Minor differences in cultural characteristics were noticed: In *S. toyocaensis* ATCC 19814 the white aerial mycelium is produced on glycerol-asparagine agar, Emerson's agar, nutrient agar, casein agar, tyrosine agar, and gelatin agar; the colonies show more wrinkles on Emerson's agar and are gray rather than gray to pink gray on inorganic salts-starch agar; sporulation is better on Czapek-sucrose agar, starch agar, potato carrot agar, and tap water agar but poorer on glucose-asparagine agar. Culture N469-34, but not *S. toyocaensis*, exhibits failure to reduce inorganic nitrate to nitrite and ability to utilize arabinose as a source of carbon. On the basis of the above-mentioned differences culture N469-34 is considered as a new subspecies of *S. toyocaensis* and named *Streptomyces toyocaensis* Nishimura, Katagiri, Sato, Mayama & Shimaoka subsp. *humicola* Huang subsp. nov. The subspecific epithet refers to its habit of living in or on soil. The culture has been deposited at the American Type Culture Collection, Rockville, Md., U.S.A., under the accession number ATCC 39471.

The permanency of the deposit of this culture at the American Type Culture Collection at Rockville, Md. and ready accessibility thereto by the public are afforded throughout the effective life of the patent in the event the patent is granted. Access to the culture is available during the pendency of the application under 37 CFR 1.14 and 35 USC 112. All restrictions on the availability to the public of the culture deposited will be irrevocably removed upon granting of the patent.

The antibiotic complex of the present invention is obtained by fermenting culture *Streptomyces toyocaensis* subsp. *humicola* (ATCC 39471) and extracting the components from the fermentation broth. Separation of said components from the extracts by classical methods such as chromatography or counter-current distribution.

Cultivation of the *Streptomyces toyocaensis* subsp. *humicola* (ATCC 39471) cultures preferably takes place in aqueous nutrient media at a temperature of 24°–32° C., and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum is prepared by scraping vegetative cells from slants or Roux bottles incubated with the N469-34 culture. A solid medium suitable for initial growth on slants and Roux bottles is ATCC medium #172.

| ATCC 172 | gms/liter |
| --- | --- |
| Glucose | 10 |
| Soluble Starch | 20 |
| Yeast Extract | 5 |
| NZ Amine A | 5 |
| Calcium Carbonate | 1 |
| Distilled Water to 1000 ml; pH to 7.0 with KOH | |
| Add Agar | 20 |

Vegetative cells from slants are used to inoculate either shake flasks or inoculum tanks; or alternately the inoculum tanks are inoculated from shake flasks. In shake flasks, growth will generally have reached its maximum in 2 to 4 days whereas in the inoculum tanks growth will usually be at the most favorable period in 1 to 3 days after inoculation. A fermentor can be inoculated with vegetative broth from the inoculum flasks or tank under completely aseptic conditions and fermented for a period of 2 to 4 days.

Shaker flasks are prepared using one of the following media.

| JDytt | g/L | MECO | g/L | FK156 PMO | g/L |
| --- | --- | --- | --- | --- | --- |
| Cerelose | 10 | Cerelose | 10 | Soluble Starch | 20 |
| Soluble Starch | 5 | Corn Starch | 20 | Cotton Seed Meal** | 5 |
| Corn Steep Liquor | 5 | Nz Amine ytt | 5 | Corn Fermentable Solids | 5 |
| Nz Amine ytt* | 5 | Wheat Germ | 5 | Dried Yeast | 2.5 |
| Calcium Carbonate | 3 | Calcium Carbonate | 4 | Corn Steep Liquor | 2.5 |
| Cobalt Chloride | 0.002 | Yeast Extract | 5 | KH$_2$PO$_4$ | 0.5 |
| pH 7.0–7.3 | | Cobalt Chloride | 0.001 | Na$_2$HPO$_4$.12H$_2$O | 0.5 |
| | | pH 7.0–7.3 | | Cobalt Chloride | 0.010 |
| | | | | pH 7.0–7.3 | |

*Sheffield Products Kraft, Inc.
**Pharmedia Traders Protein

The progress of antibiotic production during fermentation, and the bioactivity of the fermentation broth and recovery streams, can be monitored by biological assay of the broth employing a sensitive strain of *Staphylococcus aureus* or *Bacillus subtilis*. *S. aureus* ATCC 6538 and *B. subtilis* ATCC 6633 are suitable strains for this purpose. Standard plate assay technique is employed, in which the zone of inhibition surrounding a filter paper disc saturated with the broth is used as a measure of antibiotic potency. Also, thin-layer chromatography employing silica gel is a useful tool for analyzing the antibiotic produced in fermentation media and the composition of crude and purified materials extracted from the fermentation broths. The components in the broth and recovery streams can be detected by using Analtech silica gel GF plates in chloroform/methanol (9:1) and visualizing the antibiotics under ultraviolet light at 254 millimicrons. The plate can also be overlayed with agar seeded with either *S. aureus* or *B. subtilis* and incubated at 37° C. for 16 hours to detect the antibiotics.

The antibiotic complex of this invention can be recovered from a fermentation broth of *S. toyocaensis* subsp. *humicola* ATCC 39471 by extraction of the whole broth using a volatile, water-immiscible organic solvent such as ethyl acetate, n-butanol, chloroform or methylisobutyl ketone, at a pH in the range from 7 to 10. Alternatively, the mycelium can be removed from whole broth, and then the filtrate is extracted in the same manner as for whole broth. This affords a solution of the antibiotic complex in an organic solvent. The organic solvent is removed by evaporation in vacuo and the residue is stirred with hexane. The hexane is removed, leaving the antibiotic complex, usually as a solid. The crude antibiotic complex can be separated into components by chromatography or counter-current distribution.

Since the macrolide components of the antibiotic complex are neutral, they do not form acid addition salts as basic macrolides do.

The antibiotic complex of this invention shows antibacterial activity against certain gram-positive and gram-negative microorganisms. This antibacterial activity can be demonstrated by measuring the minimum inhibitory concentration (MIC) of the complex against a variety of organisms, according to standard procedures. Thus, the MIC's can be measured by the procedure recommended by the International Collaborative Study on Antibiotic Sensitivty Testing (Ericcson and Sherris, *Acta. Pathologica et Microbiologia* Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 50 mcg./ml. Single colonies are disregarded when reading plates after 18 hours at 37° C. The susceptibility (MIC) of the test organism is accepted as the lowest concentration of compound capable of producing complete inhibition of growth as judged by the naked eye.

The antibacterial activity of the antibiotic complex, and the major and two minor components of, respectively, formulae I, II and III, makes them suitable for the treatment of bacterial infections caused by susceptible organisms in mammalian subjects. In particular an antibiotic substance of this invention or a salt thereof is useful in treating bacterial infections in large farm animals, e.g., horses, cows and swine, and also domestic pets, e.g., cats and dogs.

When using an antibacterial compound of this invention, or a salt thereof, in a mammal, the compound can be administered alone, or it can be mixed with other antibiotic substances and/or pharmaceutically-acceptable carriers or diluents. Said carrier or diluent is chosen on the basis of the intended mode of administration. For example, when considering an oral mode of administration, an antibacterial compound of this invention can be used in the form of syrups, elixirs, aqueous solutions and suspensions, and the like, in accordance with standard pharmaceutical practice. The proportional ratio of active ingredient to carrier will naturally depend on the dosage contemplated; however, said proportional ratio will normally be in the range from 1:6 to 6:1 by weight, and preferably 1:1 to 1:4. An antibacterial compound of this invention can also be administered parenterally which includes intramuscular, intraperitoneal, subcutaneous and intravenous administration. For these purposes, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in pets and farm animals and the daily dosages to be used will not differ significantly from other macrolide antibiotics, such as tylosin. The prescribing veterinarian will ultimately determine the appropriate dose for a given subject, and this can be expected to vary according to the weight and response of the individual animal as well as the nature and severity of the animal's symptoms. The compounds of this invention will normally be used orally at dosages in the range from 20 to about 50 mg. per kilogram of body weight per day, and parenterally at dosages from about 10 to about 30 mg. per kilogram of body weight per day, usually in divided doses. In some instances it may be necessary to use doses outside these ranges.

The following examples are provided solely for further illustration.

EXAMPLE 1

Twenty pots were prepared with JDytt medium, 3 liters of medium per pot. One milliliter of L61 was added as antifoaming agent, and the vessels sealed and sterilized at 120° C. and 15 p.s.i. for 45 minutes. The pots were inoculated with 3% inoculum, fermented for 1 to 3 days at 30° C., with stirring at 1700 revolutions per minute (RPM) and air sprayed through the broth at one volume per volume per minute. When fermentation is complete (based on antibiotic disc assay versus *Micrococcus luteus* ATCC 9341 or *B. subtilis* ATCC 6633) the fermentors were stopped and extracted with ⅓ volume of methylisobutyl ketone. The solvent layer was separated by means of an alpha DeLaval LAPX202 separator and the solvent concentrated to a thin syrup. The concentrate was poured with stirring into 10–20 volumes of heptane, then decanted. The residue was dissolved in methanol and passed down a Pharmacia LH-20 Sephadex column in methanol. The gram-positive bioactive fractions were collected, concentrated and rechromatographed on a $C_{18}$ partisil reverse phase column. The elution of the macrolide antibiotics was followed by bioassay and tlc (vanillin reagent). The active fractions were combined based on the tlc and biopotency of the cuts in order to separate the individual components. CP-63,693, CP-64,537 and CP-64,593 cuts were combined, concentrated and recovered from solution as crystalline or amorphous solids.

The bioactivity of the broth, extracts and column cuts can be followed by using a sensitive strain of *Bacillus subtilis* ATCC 6633, *Staphylococcus aureus* ATCC 6538, or *Micrococcus luteus* ATCC 9341. The individual components in the broth, extracts or column cuts can be visualized by using Analtech silica gel GF plates in the following systems neat ethyl acetate, chloroform/methanol 9:1 or 3:1 v/v or chloroform/acetone/ammonium hydroxide 25:25:1 v/v/v and spraying the developed plates with vanillin reagent (5 grams vanillin in 100 ml. of ethanol and 50 ml. of 85% phosphoric acid). The plates are heated to 80° C. and the antibiotics appear gray to blue/purple on a white background. The individual components can also be visualized by overlaying the developed plate with the bacterial organisms aforementioned in agar, adding tetrazolium and incubating the plates overnight at 37° C. The antibiotics will appear as clear zones against a reddish background.

EXAMPLE 2

Scale-up in large fermentors (25 to 1000 gallons) was carried out by preparing large shake flasks containing 0.7 liters of JDytt or FK-156 PMO medium. The shake flask inoculum was fermented 2 to 4 days at 28° C., and used to inoculate a 50, 250 or 1500 gallon fermentor containing 25, 100 or 1000 gallons of medium. The fermentors were harvested at 2 to 4 days.

A 1000 gallon fermentor was recovered by extracting the whole broth at natural pH with 300 gallons of methylisobutyl ketone (MIBK). The MIBK extract was separated from the water layer on a Podbielniak centrifugal extractor and concentrated to approximately 4 liters. The concentrate was defated with heptane, then dissolved (300 ml. aliquots at a time) in methanol and passed down 3 liters of sephadex LH-20 in methanol. The gram-positive bioactive cuts were collected, combined and concentrated in vacuo to a thin syrup. The residue was chromatographed on a $C_{18}$ partisil prep column. The fractions were followed by tlc and bioassay. CP-63,693, CP-64,537 and CP-64,593 were identified in the cuts by tlc and selectivity combined, concentrated and the individual macrolides recovered as crystalline or amorphous solids yielding gram quantities of each compound.

EXAMPLE 3

The procedure of Example 2 was repeated providing approximately 350 gallons of methylisobutyl ketone extract of whole broth (ca. 1100 gallons) which was separated on a Podbielniack extractor and concentrated in vacuo to give six liters of a black oil containing the antibiotic complex. One liter of the oil was poured slowly into twelve liters of hexane which was stirring vigorously. After stirring thirty minutes the hexane was decanted away from an insoluble oil. The oil representing greater than ninety percent of the original bioactivity was dissolved in methanol, transferred to a tared round bottom flask and concentrated in vacuo to an oil weighing approximately 150 grams. Fifty grams of the above oil was then dissolved in 250 milliliters of methanol and added to two liters of Pharmacia Sephadex LH-20, preswollen in methanol and packed in a glass column 10 centimeters in diameter by seventy centimeters long. The column was developed with methanol and, when the color neared the base of the column, twenty milliliter cuts were collected. The cuts may be analyzed by bio-assay or bio-overlay or preferably by spot test followed by tlc and vanillin spray. The cuts containing the macrolide antibiotics were combined and concentrated in vacuo to yield approximately ten grams of a light tan semi-solid.

Ten grams of the semi-solid were dissolved in chloroform and added to a glass column containing 250 grams of silica gel 60 (70–230 mesh) one inch in diameter by ninety-six centimeters high in hexane. The column was eluted with hexane, hexane:chloroform 50:50, then chloroform followed by elution with a gradient of chloroform to chloroform:acetone 50:50. After 1.5 liters of forecuts were collected as a single fraction, twenty milliliter cuts were collected when the color neared the base of the column. All cuts from the purification sequence were monitored by thin layer chromatography vida ut supra. The greater part of the antibiotic activity was found as the solvent mixture approached 50:50 chloroform:acetone. The appropriate cuts were combined and evaporated in vacuo to a foam yielding approximately four grams.

Four grams of the foam were dissolved in methanol and stirred gram per gram with Darco G60 carbon for sixty minutes. The carbon was removed by filtration and the volume reduced under vacuum to forty milliliters, then sixty milliliters of water is added to a hazy solution. This solution is filtered through a Nylon 66 0.2 micron filter and pumped onto a Whatman Partisil Magnum (M-20) 10/50 ODS 3 column equipped with a 12 millimeter in diameter by fifteen centimeter high guard column also packed with ODS 3. The column was eluted with three liters of methanol:water 40:60 to remove the last of a yeast active contaminent which had been carried along during the process recovery. The elution of the macrolides is carried out with methanol:water 60:40 with twenty milliliter cuts being collected. Thin layer chromatography of the reverse phase column cuts show CP-64,537 to be eluted first yielding 1.3 grams in cuts 10 to 19. CP-63,693 appears next yielding 0.4 grams in cuts 21 to 26 and CP-64,593 yielding 0.6 grams in cuts 31 to 40. CP-63,693 was crystallized from hot heptane and collected by filtration. CP-64,537 and CP-64,593 have resisted crystallization and were sent for biological and physico-chemical test as amorphous solids. All samples before analysis, were dried for four hours at 56° C. under high vacuum. They exhibit the same solubility being soluble in methanol, ethanol, chloroform, ethylene chloride, acetone, methylisobutyl ketone, and insoluble in heptane, hexane and water.

| CP-63,693 | | Mp 158–160° C. |
|---|---|---|
| Elemental analysis | $C_{48}H_{82}O_{20}$ | M.W. 979.136 |
| Calculated | Found | Found |
| C 58.87% | C 58.64% | C 58.62% |
| H 8.44% | H 8.29% | H 8.31% |
| O 32.68% | O 33.01% by difference | O 33.07% by difference |
| | $[alpha]_D^{25°} = -70.2$ (c 1 MeOH) | |

The ultraviolet absorption in methanol only exhibits slight end absorption. The infrared spectrum (KBr disc) of CP-63,693 exhibits distinguishable bands in the infrared spectrum over the region 2 to 14 microns which are as follows:

2.88, 2.92, 3.36, 3.40, 3.47, 5.78 (sh), 5.79 (sh), 5.84, 6.85, 7.25, 7.48, 8.15, 8.61, 8.99, 9.28, 1.00, 12.8.

| CP-64,537 | | Mp 98–100° C. |
|---|---|---|
| Elemental analysis | $C_{42}H_{74}O_{17}$ | M.W. 851.12 |
| Calculated | Found | Found |
| C 59.27% | C 59.52% | C 59.09% |
| H 8.76% | H 8.65% | H 8.59% |
| O 31.96% | O 31.83% by difference | O 32.32% by difference |
| | $[alpha]_D^{25°} = -62.5$ (c 1 MeOH) | |

The ultraviolet absorption in methanol only exhibits slight end absorption. The infrared spectrum (KBr disc) of CP-64,537 exhibits distinguishable bands in the infrared spectrum over the region 2 to 14 micron which are as follows:

2.8, 3.36, 3.41, 3.47, 3.53, 5.75, 5.83, 6.85, 7.25, 8.57, 9.22, 9.45, 1.00, 1.27.

| CP-64,593 | | Mp 118–128° C. |
|---|---|---|
| Elemental analysis | $C_{42}H_{47}O_{17}$ | M.W. 851.12 |
| Calculated | Found | Found |
| C 59.27% | C 58.86% | C 58.88% |
| H 8.76% | H 8.68% | H 8.66% |
| O 31.96% | O 32.46% by difference | O 32.46% by difference |
| | $[\alpha]_D^{25°} = -39.3$ (c 1 MeOH) | |

The ultraviolet absorption in methanol only exhibits slight end absorption. The infrared spectrum (KBr disc) of CP-64,593 exhibits distinguishable bands in the infrared spectrum over the region 2 to 14 microns which are as follows:

2.86, 3.36, 3.41, 5.76, 6.85, 7.23, 8.55, 9.23, 9.41, 9.96, 1.27.

We claim:

1. A biologically pure culture of the microorganism *Streptomyces toyocaensis* subsp. *humicola* Huang subsp. nov. ATCC 39471, said culture being capable of producing neutral macrolides which have a keto sugar and contain a 2-hydroxyisovaleryl moiety in their structure, in a recoverable quantity, upon cultivation in an aqueous nutrient medium containing assimilable sources of nitrogen and carbon.

* * * * *